US012564558B2

(12) United States Patent
Sood et al.

(10) Patent No.: US 12,564,558 B2
(45) Date of Patent: Mar. 3, 2026

(54) HYBRID EXOSOMAL-POLYMERIC (HEXPO) NANO-PLATFORM FOR DELIVERY OF RNAI THERAPEUTICS

(71) Applicant: Board of Regents, The University of Texas System, Austin, TX (US)

(72) Inventors: Anil K. Sood, Pearland, TX (US); Sherry Y. Wu, Houston, TX (US); Gabriel Lopez-Berestein, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 974 days.

(21) Appl. No.: 16/467,401

(22) PCT Filed: Dec. 8, 2017

(86) PCT No.: PCT/US2017/065371
§ 371 (c)(1),
(2) Date: Jun. 6, 2019

(87) PCT Pub. No.: WO2018/107061
PCT Pub. Date: Jun. 14, 2018

(65) Prior Publication Data
US 2020/0069594 A1 Mar. 5, 2020

Related U.S. Application Data

(60) Provisional application No. 62/432,236, filed on Dec. 9, 2016.

(51) Int. Cl.
| | |
|---|---|
| *A61K 9/50* | (2006.01) |
| *A61K 9/00* | (2006.01) |
| *A61K 9/51* | (2006.01) |
| *C12N 15/113* | (2010.01) |

(52) U.S. Cl.
CPC .......... *A61K 9/5015* (2013.01); *A61K 9/0019* (2013.01); *A61K 9/5138* (2013.01); *A61K 9/5161* (2013.01); *C12N 15/1135* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 9,085,778 B2 | 7/2015 | Lotvall et al. | |
| 2012/0315324 A1* | 12/2012 | Zhang .................. | A61K 33/243 514/274 |
| 2013/0315937 A1 | 11/2013 | Lee et al. | |
| 2015/0118288 A1 | 4/2015 | Lee | |
| 2016/0158291 A1 | 6/2016 | Kreke et al. | |

FOREIGN PATENT DOCUMENTS

| | | | |
|---|---|---|---|
| WO | WO 2010/119256 | | 10/2010 |
| WO | WO 2013/070324 | | 5/2013 |
| WO | WO 2013/138930 | * | 9/2013 |
| WO | WO 2016/033695 | | 3/2016 |

OTHER PUBLICATIONS

Admyre et al. (J Immunol., 2007, 179(3), 1969-1978) (Year: 2007).*
Shtam et al. (Cell Communication and Signaling, 2013, 11, 88) (Year: 2013).*
Perez-Bermudez et al. (Extracellular vesicles in food: experimental evidence of their secretion in grape fruits, accepted: Sep. 15, 2016). (Year: 2016).*
"ExoFectin® sRNA-into-Exosome Kit (Chemical)," retrieved at http://www.101bio.com/files/manual_P401%20ExoFectin-Chem. pdf, downloaded Apr. 2016.
Alvarez-Erviti et al., Delivery of siRNA to the mouse brain by systemic injection of targeted exosomes. Nature Biotechnology, 29:341-345, 2011.
Cooper et al., Systemic exosomal siRNA delivery reduced alpha-synuclein aggregates in brains of transgenic mice. Movement Disorders, 29:1476-1485, 2014.
Ishii et al., "Mechanism of cell transfection with plasmid/chitosan complexes," *Biochimica et Biophysica Acta*, 1514:51-64, 2001.
Ju et al., "Grape exosome-like nanoparticles induce intestinal stem cells and protect mice from DSS-induced colitis," *Molecular Therapy*, 21(7):1345-1357, 2013.
Kooijmans et al., "Electroporation-induced siRNA precipitation obscures the efficiency of siRNA loading into extracellular vesicles," *J. Control Release*, 172:229-238, 2013.
Lavertu et al., "High efficiency gene transfer using chitosan/DNA nanoparticles with specific combinations of molecular weight and degree of deacetylation," *Biomaterials*, 27:4815-4824, 2006.
PCT International Search Report and Written Opinion issued in International Application No. PCT/US2017/065371, mailed Feb. 12, 2018.
Peterson et al., "Integrated systems for exosome investigation," *Methods*, 87:31-45, 2015.
Salama et al., "MicroRNA-29b modulates innate and antigen-specific immune responses in mouse models of autoimmunity," *PLoS One*, 9(9):e106153, 2014.
Shtam et al., "Exosomes are natural carriers of exogenous siRNA to human cells in vitro," *Cell Commun Signal*, 11(88):1-10, 2013.
Sorgi et al., "Protamine sulfate enhances lipid-mediated gene transfer," *Gene Therapy*, 4:961-968, 1997.
Wahlgreen et al., "Plasma exosomes can deliver exogenous short interfering RNA to monocytes and lymphocytes," *Nucleic Acids Research*, 40(17):e130, 2012.
Xu et al., "Polymeric carriers for gene delivery: chitosan and poly(amidoamine) dendrimers," *Curr Pharm Des.*, 16(21):2350-2368, 2010.

(Continued)

*Primary Examiner* — Genevieve S Alley
(74) *Attorney, Agent, or Firm* — pH IP Law

(57) ABSTRACT
Provided herein are lipid-based nanoparticles (e.g., exosomes) having (a) a core comprising a cationic polymer and a therapeutic agent (e.g., a therapeutic protein, an antibody, an inhibitory RNA, and/or a small molecule drug) and (b) a lipid coating comprising an exosomes-derived membrane. Furthermore, the present invention provides methods of producing such nanoparticles as well as methods for use of such lipid-based nanoparticles in therapy.

16 Claims, 12 Drawing Sheets

(56) References Cited

OTHER PUBLICATIONS

Yang et al., "Delivery of Small Interfering RNA to Inhibit Vascular Endothelial Growth Factor in Zebrafish Using Natural Brain Endothelia Cell-Secreted Exosome Nanovesicles for the Treatment of Brain Cancer," *AAPS J*, 19(2):475-486, 2016.

Corvigno et al., "Enhancing plant-derived vesicles for nucleotide delivery for cancer therapy," npj Precision Oncology 8:86, pp. 1-13, 2024.

* cited by examiner

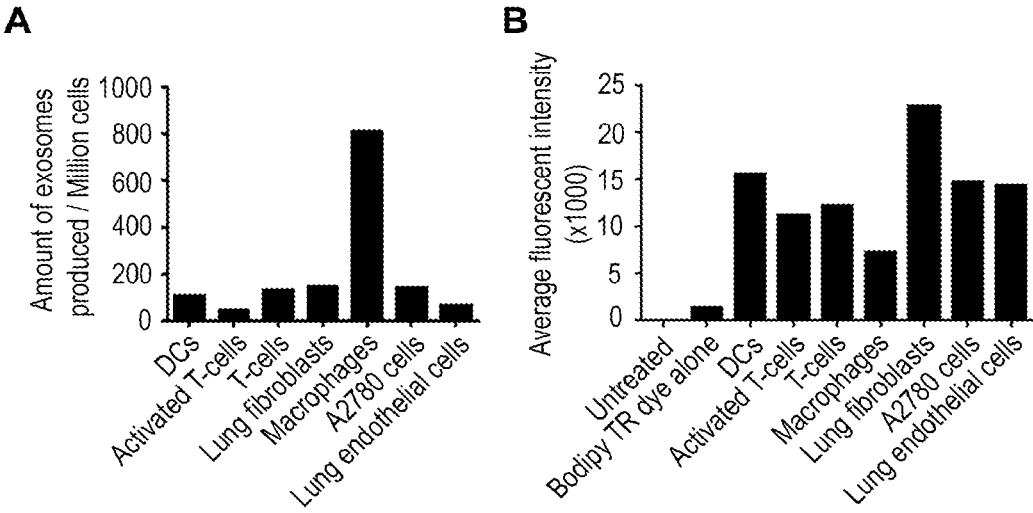
FIGS. 1A-B

ExoFect-loaded Exosomes   Lipofectamine-loaded Exosomes   HEXPO Nanoparticles

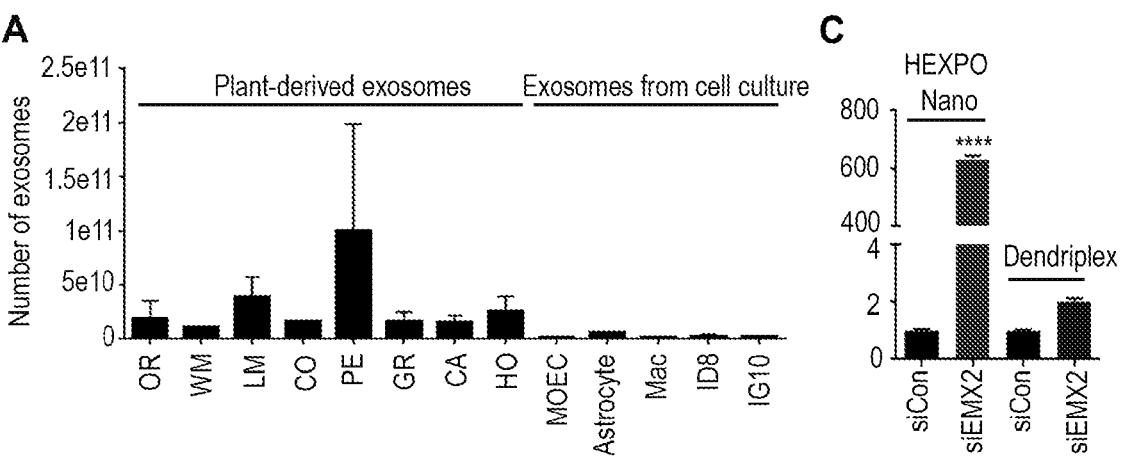
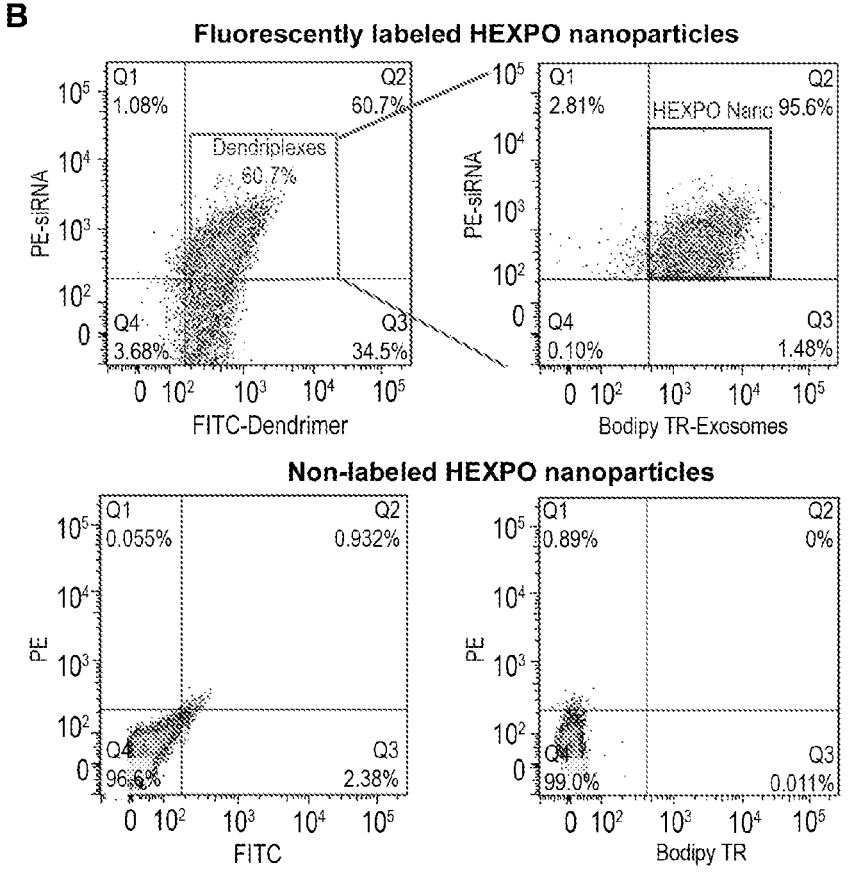
FIGS. 12A-C

HYBRID EXOSOMAL-POLYMERIC (HEXPO) NANO-PLATFORM FOR DELIVERY OF RNAI THERAPEUTICS

The present application is a national phase application under 35 U.S.C. § 371 of International Application No. PCT/US2017/065371, filed Dec. 8, 2017, which claims the priority benefit of U.S. provisional application No. 62/432,236, filed Dec. 9, 2016, the entire contents of each of which are incorporated herein by reference.

BACKGROUND OF THE INVENTION

1. Field of the Invention

The present invention relates generally to the field of medicine. More particularly, it concerns methods of transfecting isolated exosomes with therapeutic molecules, transfected exosomes produced according to said methods, and methods of treating a patient with said exosomes.

2. Description of Related Art

Therapeutic applications of RNAi nucleotides have been limited by poor tumoral delivery and intracellular uptake as well as rapid enzymatic degradation. Exosomes are naturally occurring nano-sized vesicles that can protect RNA from enzyme degradation and can efficiently deliver cargo to recipient cells. The use of exosomes for RNAi nucleotide delivery has been previously described in the literature (Alvarez-Erviti, 2011; Cooper, 2014). However, these studies rely on the use of freshly isolated cells to produce exosomes. This method of preparation is labor intensive and cost inefficient. Moreover, while the RNAi nucleotide loading efficiency was originally reported to be about 30% (Alvarez-Erviti, 2011), a recent paper from the same research group describes the presence of extensive siRNA aggregate formation after electroporation, the method used for RNAi nucleotide loading in that study (Kooijmans et al., 2013). These aggregates cause an overestimation of the amount of siRNA actually loaded into exosomes; the true loading efficiency was only about 0.05% (Kooijmans et al., 2013). Key challenges such as difficulty of loading therapeutic payload efficiently into exosomes and inability to scale up their production has significantly hindered the clinical translation of this technology.

SUMMARY OF THE INVENTION

Here, methods are provided to (a) produce exosomes in large quantities, and (b) load RNAi polynucleotides into exosomes with high efficiency (>95%). The disclosed Hybrid EXosomal-POlymeric (HEXPO) nanoparticles are mono-dispersed and have an average size of around 140 nm. These HEXPO nanoparticles can deliver RNAi nucleotides efficiently into tumor cells and localize in tumors following systemic administration.

In one embodiment, pharmaceutical compositions are provided comprising a lipid-based nanoparticle and an excipient, wherein the lipid-based nanoparticle comprises (a) a core comprising a cationic polymer and a therapeutic agent and (b) a lipid coating comprising an exosomes-derived membrane.

In one aspect, the lipid-based nanoparticle comprises an exosomes. In some aspects, the exosomes are isolated from a mammalian cell or a plant. In certain aspects, the plant is a fruit. In various aspects, the fruit is a orange, watermelon, lemon, peach, grape, cantaloupe, honeydew, apple, tomato, pear, or a grapefruit.

In some aspects, the cationic polymer is PAMAM (e.g., G3-PAMAM or G4-PAMAM), chitosan, or protamine.

In some aspects, the therapeutic agent is a nucleic acid, a therapeutic protein, an antibody, or a small molecule drug. In some aspects, the therapeutic agent is a nucleic acid. In some aspects, the nucleic acid is a plasmid DNA. In some aspects, the nucleic acid is an inhibitory RNA. In some aspects, the inhibitory RNA is a siRNA, shRNA, miRNA, or pre-miRNA.

In certain aspects, the nitrogen:phosphate ratio is between about 6 and about 50. In some aspects, the compositions further comprise sucrose. In some aspects, the exosomes:nucleic acid ratio is about 10-15 billion exosomal particles per 15 µg of nucleic acid.

In some aspects, the composition is formulated for parenteral administration. In some aspects, the composition is formulated for intravenous, intramuscular, sub-cutaneous, or intraperitoneal injection.

In one embodiment, methods are provided of transfecting isolated exosomes comprising: (a) incubating the therapeutic agent with a cationic polymer to produce a polyplex; and (b) incubating the polyplex with isolated exosomes, thereby transfecting the isolated exosomes with the therapeutic agent.

In some aspects, the cationic polymer is PAMAM (e.g., G3-PAMAM or G4-PAMAM), chitosan, or protamine. In certain aspects, the isolated exosomes are isolated from mammalian cells. In certain aspects, the isolated exosomes are isolated from plant cells.

In certain aspects, the therapeutic agent is a nucleic acid, a therapeutic protein, an antibody, or a small molecule drug. In some aspects, the therapeutic agent is a nucleic acid. In some aspects, the nucleic acid is an inhibitory RNA. In some aspects, the nitrogen:phosphate ratio is between about 6 and about 50. In some aspects, the exosomes:nucleic acid ratio is about 10-15 billion exosomal particles per 15 µg of nucleic acid.

In certain aspects, the transfected exosomes have a uniform particle size distribution. In certain aspects, the transfected exosomes are about 135 nm in diameter.

In one embodiment, transfected exosomes produced according to the methods of the present embodiments are provided. In one aspect, the transfected exosomes are a lyophilized composition.

In one embodiment, pharmaceutical compositions are provided comprising a transfected exosomes according to the present embodiments and an excipient. In some aspects, the compositions further comprise sucrose. In some aspects, the sucrose:nucleic acid ratio is isotonic. In some aspects, the composition is formulated for parenteral administration. In some aspects, the composition is formulated for intravenous, intramuscular, sub-cutaneous, or intraperitoneal injection.

In one embodiment, methods are provided for treating a disease in a patient in need thereof comprising administering a composition of the present embodiments to the patient, thereby treating the disease in the patient. In one embodiment, a composition of the present embodiments is provided for use in treating a disease in a patient in need thereof. In some aspects, the disease is a cancer. In some aspects, the cancer is ovarian cancer. In some aspects, the therapeutic agent is an inhibitory RNA targeting an oncogene. In some aspects, the methods further comprise administering at least a second therapy to the patient. In some aspects, the second therapy comprises a surgical therapy, chemotherapy, radiation therapy, cryotherapy, hormonal therapy, or immunotherapy. In some aspects, the patient is a human.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B. Isolation and delivery efficiency of exosomes. FIG. 1A. Amount of exosomes generated by different types of conditionally immortalized murine cells. Quantification was performed by measuring protein concentration of isolated exosomes. FIG. 1B. Uptake of Bodipy TR-labeled exosomes into A2780 ovarian cancer cells.

FIG. 2A. Transfection efficiency was assessed 24 hours post transfection. The left bar of each pair represents siControl; the right bar of each pair represents siEMX2. FIG. 2B. Cell viability was assessed using the MTT assay. Lipofectamine transfection reagent was used as a positive control (n=3 for all assays).

4

Figure 4:
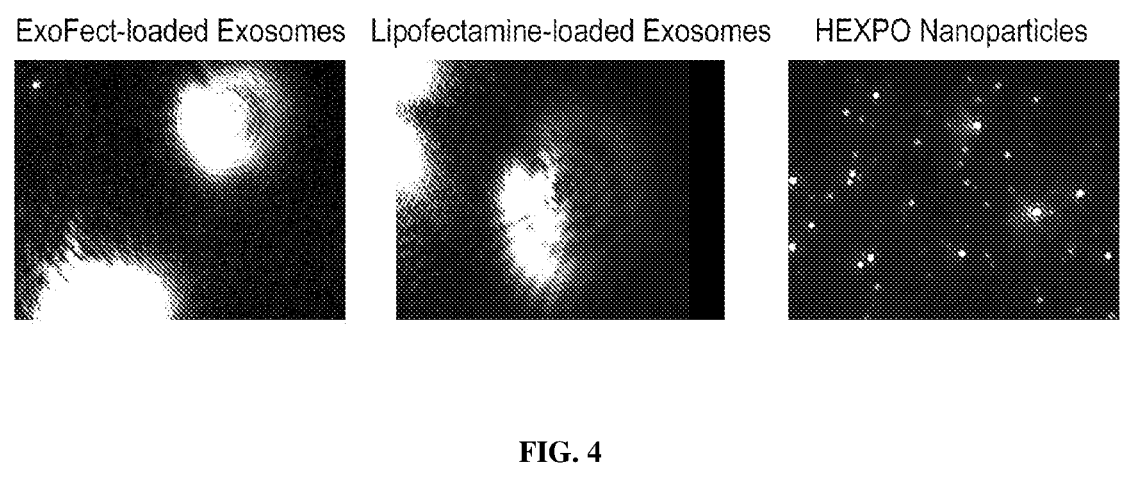

FIG. 4. Bright field images of the particles in the Nano-Sight NTA software. The Brownian motion of each particle is shown.

Figure 5:
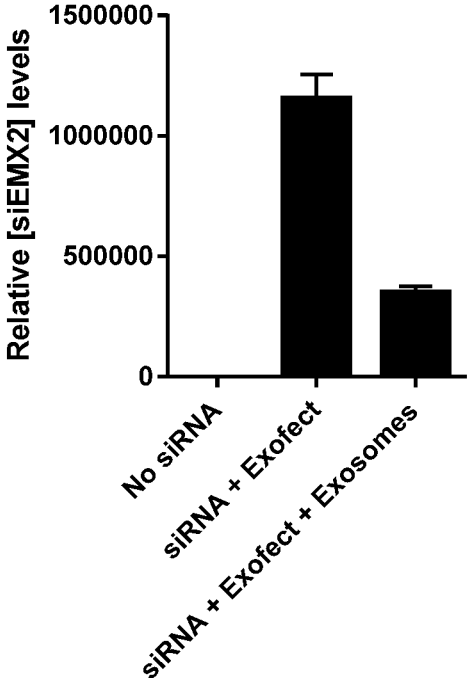

FIG. 5. siRNA levels in (1) no siRNA control, (2) Exofect complexed siRNA, and (3) Exofect/siRNA-loaded exosomes samples following ExoQuick treatment. SiRNA levels were determined in the precipitated pellets via stem-loop PCR.

Figure 6:
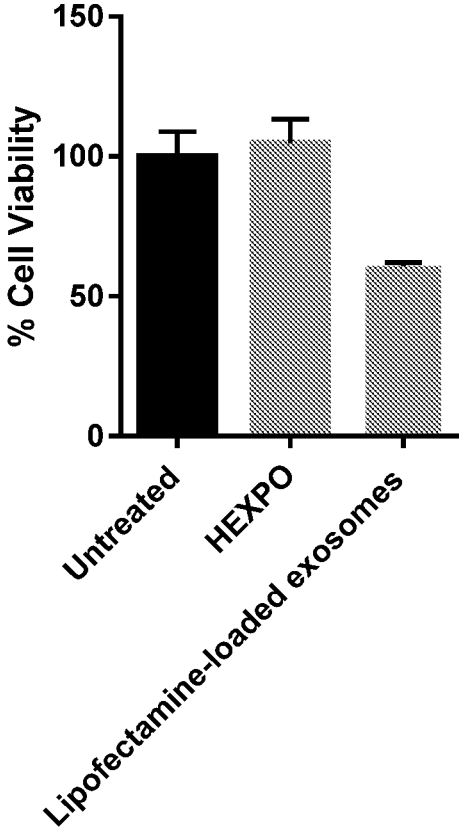

FIG. 6. Effect of HEXPO and Lipofectamine-loaded exosomes on cell viability (n=3).

Figure 7:
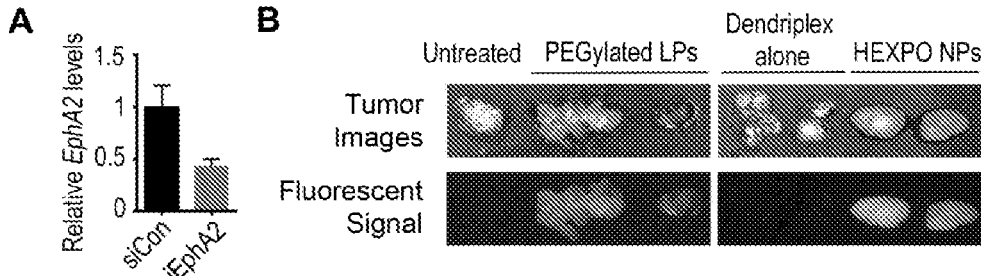

FIGS. 7A-B. Delivery of siRNAs using HEXPO nanoparticles. FIG. 7A. Knockdown of EphA2 in human ovarian cancer cells using siEphA2-containing HEXPO nanoparticles. FIG. 7B. Delivery of DiR-labeled PEGylated liposomes and HEXPO nanoparticles to tumors in A2780 mouse model of ovarian cancer. All mice received one dose of therapy.

Figure 8:
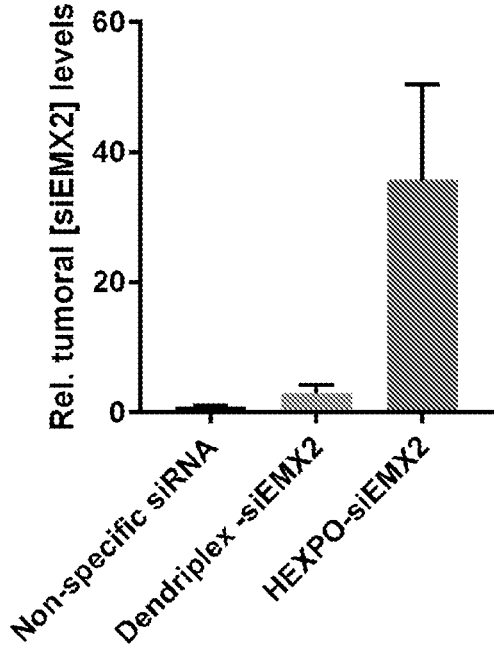

FIG. 8. Relative level of siEMX2 detected in ID8 tumors treated with (1) non-specific siRNA, (2) siEMX2-containing HEXPO nanoparticles without exosomal membrane (Dendriplex), and (3) siEMX2-containing HEXPO nanoparticles coated with exosomal membrane. SiRNAs were administered i.p. into mice bearing ID8 tumors (5 μg siRNA/mouse) and mice were sacrificed 24 hours post treatment. Level of siRNAs in tumors was assessed by the stemloop PCR technique. Two mice were examined in each treatment group.

Figure 9:
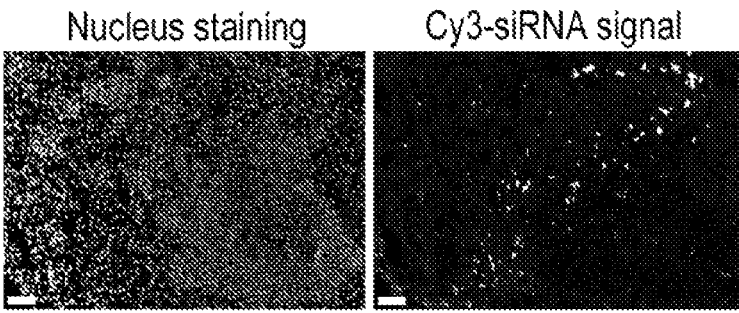

FIG. 9. Penetration of HEXPO nanoparticles in tumors. Mice bearing ID8 tumors were treated with one dose of Cy3-siRNA containing HEXPO nanoparticles (i.p., 5 μg siRNA). Fluorescence microscopy was used to identify the location of siRNAs in tumors 24 hours post treatment.

Figure 10:
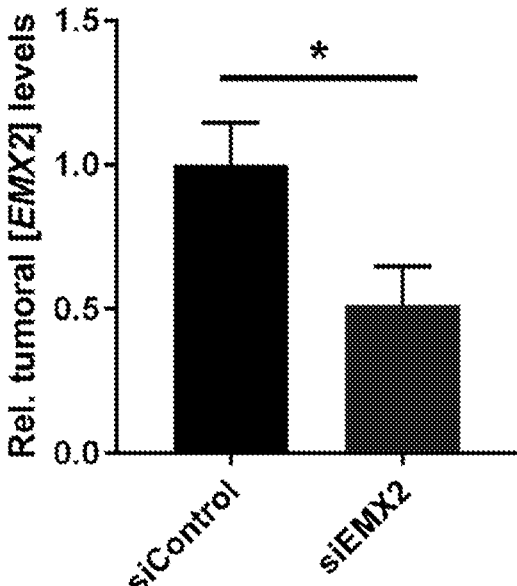

FIG. 10. Knockdown of EMX2 in ID8 tumors following HEXPO nanoparticle treatment. Mice bearing ID8 tumors were treated with 3 doses of HEXPO-siControl or HEXPO-siEMX2 (i.p., 5 μg siRNA/dose), 3 days apart. The extent of gene knockdown in tumors was assessed 48 hours post the last dose. Five mice were examined in each treatment group.

Figure 11:
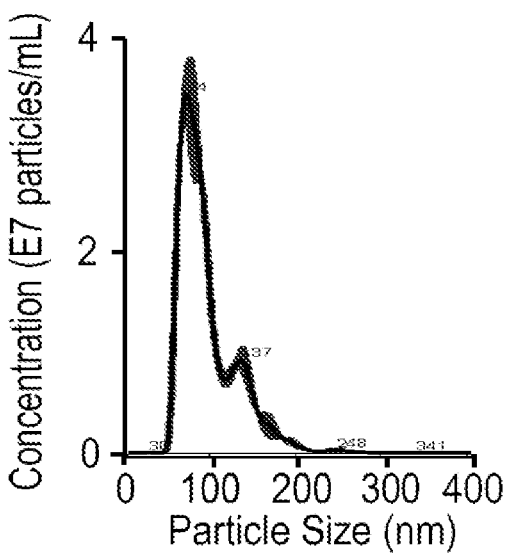

FIG. 11. Particle size distribution of lyophilized HEXPO nanoparticles. Lyophilized HEXPO nanoparticles are suitable for long-term storage and can be hydrated immediately before use.

FIGS. 12A-C. Formulation of siRNA-loaded HEXPO nanoparticles using plant-derived exosomes. FIG. 12A. The number of exosomes that can be generated from 1 mL of juice or 1 million cultured cells. OR, orange; WM, watermelon; LM, lemon; CO, corn; PE, peach; GR, grapes; CA, cantaloupe; HO, honeydew; Mac, macrophages; ID8, murine ID8 ovarian cancer cells; IG10, murine IG10 ovarian cancer cells. FIG. 12B. Loading of siRNAs into plant-derived exosomes. PE-labeled siRNA (5 μg) was loaded into Bodipy TR-labeled watermelon-derived exosomes. FITC-labeled PAMAM dendrimer was used to complex with the siRNA before loading. Loading efficiency was assessed via flow cytometry. FIG. 12C. Delivery of siEMX2 into murine endothelial cells by using HEXPO nanoparticles formulated using watermelon-derived exosomes. ****, P<0.0001, compared with dendrimer complexed siEMX2.

DESCRIPTION OF ILLUSTRATIVE EMBODIMENTS

Exosomes are naturally occurring vesicles (about 50-100 nm) that facilitate effective cell-to-cell communication in the body. Exosomes are highly stable in biological fluids, can protect RNA from enzyme degradation, and can efficiently deliver their cargo to recipient cells. Of importance, vesicles composed solely of lipids in the ratios found in exosomes are unable to fuse with cells, indicating the critical roles that exosomal surface proteins play in cell entry. These exosomal surface proteins dominate the uptake efficiency of exosomes in specific organs and cell types. Exosomes can be further engineered to express desired ligands (e.g., lamp2b-RVG) on the membrane surface, which permits active tumor targeting. Being natural transporters, exosomes are also less likely to exert toxicity or elicit immune responses. These unique properties make them ideal candidates for drug delivery. However, although some studies have reported the use of exosomes for delivering RNAi nucleotides or chemotherapeutic agents, key challenges (e.g., loading efficiency (typically 2%-3%), inability to scale up production, and the need to deplete pre-existing exosomal content prior to loading) remain for translating this technology into the clinic. Provided herein are methods to address several of these issues, including generation of the innovative Hybrid EXosomal-POlymeric (HEXPO) nano-platform, which permits high siRNA loading efficiency combined with high tumor-targeting capability.

As such, novel methods are provided herein to (a) produce exosomes in large quantities and (b) to load RNAi nucleotides into exosomes with high efficiency. Production of exosomes using the methods disclosed herein is significantly less expensive and the resultant exosomal particles are safe for human use. In addition, methods are provided to isolate large quantities of exosomes from plants. The cost of exosomes production using the disclosed method is approximately 4000-fold lower than the cost required to generate exosomes from cells growing in culture. Using these exosomes, an innovative Hybrid EXosomal-POlymeric (HEXPO) nano-platform is provided, which preserves the targeting ability of exosomal membranes while containing a polymeric core that enables efficient RNAi polynucleotide loading. The disclosed methods of producing HEXPO nanosystems also addresses the loading efficiency issue. HEXPO nanoparticles, which consist of polymeric cores with exosomal membranes, are provided using plant-derived exosomes. This design preserves the targeting ability of exosomal membranes while ensuring high loading efficiency (>95% loading efficiency). The use of polymers to facilitate loading of RNAi nucleotides into exsosomes has not been previously described. It was previously unknown whether the presence of negatively-charged exosomal membrane would disrupt polymer-nucleotide interaction or vice versa. As provided by the formulation conditions defined herein, efficient loading can be achieved without compromising the integrity of the exosomal membrane.

Aspects of the present disclosure can be used to produce exosomes-based pharmaceuticals for the treatment of a variety of human diseases. The formulation method disclosed herein can be applied to different types of therapeutics, including RNAi polynucleotides, anti-cancer therapeutics, and imaging agents. In addition, the methods of exosome production can be used to generate large quantities of exosomes. These exosomes enable targeted therapy for the treatment of a wide range of diseases.

I. EXOSOMES

The terms "microvesicle" and "exosomes," as used herein, refer to a membranous particle having a diameter (or largest dimension where the particle is not spheroid) of between about 10 nm to about 5000 nm, more typically between 30 nm and 1000 nm, and most typically between about 50 nm and 750 nm, wherein at least part of the membrane of the exosomes is directly obtained from a cell. Most commonly, exosomes will have a size (average diameter) that is up to 5% of the size of the donor cell. Therefore, especially contemplated exosomes include those that are shed from a cell.

Exosomes may be detected in or isolated from any suitable sample type, such as, for example, body fluids. As used herein, the term "isolated" refers to separation out of its natural environment and is meant to include at least partial purification and may include substantial purification. As used herein, the term "sample" refers to any sample suitable for the methods provided by the present invention. The sample may be any sample that includes exosomes suitable for detection or isolation. Sources of samples include blood, bone marrow, pleural fluid, peritoneal fluid, cerebrospinal fluid, urine, saliva, amniotic fluid, malignant ascites, broncho-alveolar lavage fluid, synovial fluid, breast milk, sweat, tears, joint fluid, and bronchial washes. In one aspect, the sample is a blood sample, including, for example, whole blood or any fraction or component thereof. A blood sample suitable for use with the present invention may be extracted from any source known that includes blood cells or components thereof, such as venous, arterial, peripheral, tissue, cord, and the like. For example, a sample may be obtained and processed using well-known and routine clinical methods (e.g., procedures for drawing and processing whole blood). In one aspect, an exemplary sample may be peripheral blood drawn from a subject with cancer.

Exosomes may also be isolated from tissue samples, such as surgical samples, biopsy samples, tissues, feces, and cultured cells. When isolating exosomes from tissue sources it may be necessary to homogenize the tissue in order to obtain a single cell suspension followed by lysis of the cells to release the exosomes. When isolating exosomes from tissue samples it is important to select homogenization and lysis procedures that do not result in disruption of the exosomes. Exosomes contemplated herein are preferably isolated from body fluid in a physiologically acceptable solution, for example, buffered saline, growth medium, various aqueous medium, etc.

In some embodiments, the exosomes are isolated from the tissues or juices of fruit (e.g., grape, grapefruit, watermelon, and tomatoes). It has now been discovered that edible plants, such as fruits, are not only a viable source of large quantities of exosomes, but that exosomes derived from edible plants can be used as an effective delivery vehicle for a number of therapeutic agents, while also retaining the biological activity of the therapeutic agents. See PCT Publication No. WO2012/070324. The presently-disclosed subject matter thus includes edible plant-derived exosomes compositions that further include therapeutic agents and are useful in the treatment of various diseases. In some embodiments of the presently-disclosed subject matter, an exosomes composition is provided that comprises a therapeutic agent encapsulated by an exosomes, wherein the exosomes is derived from an edible plant.

The term "edible plant" is used herein to describe organisms from the kingdom Plantae that are capable of producing their own food, at least in part, from inorganic matter through photosynthesis, and that are fit for consumption by a subject, as defined herein below. Such edible plants include, but are not limited to, vegetables, fruits, nuts, and the like. In some embodiments of the exosomes compositions described herein, the edible plant is a fruit. In some embodiments, the fruit is selected from a grape, a grapefruit, a watermelon, and a tomato.

The phrase "derived from an edible plant," when used in the context of an exosomes derived from an edible plant, refers to an exosomes that, by the hand of man, exists apart from its native environment and is therefore not a product of nature. In this regard, in some embodiments, the phrase "derived from an edible plant" can be used interchangeably with the phrase "isolated from an edible plant" to describe an exosomes of the presently-disclosed subject matter that is useful for encapsulating therapeutic agents.

Exosomes may be isolated from freshly collected samples or from samples that have been stored frozen or refrigerated. In some embodiments, exosomes may be isolated from cell culture medium. Although not necessary, higher purity exosomes may be obtained if fluid samples are clarified before precipitation with a volume-excluding polymer, to remove any debris from the sample. Methods of clarification include centrifugation, ultracentrifugation, filtration, or ultrafiltration. Most typically, exosomes can be isolated by numerous methods well-known in the art. One preferred method is differential centrifugation from body fluids or cell culture supernatants. Exemplary methods for isolation of exosomes are described in (Losche et al., 2004; Mesri and Altieri, 1998; Morel et al., 2004). Alternatively, exosomes may also be isolated via flow cytometry as described in (Combes et al., 1997).

One protocol for isolation of exosomes includes ultracentrifugation, often in combination with sucrose density gradients or sucrose cushions to float the relatively low-density exosomes. Isolation of exosomes by sequential differential centrifugations is complicated by the possibility of overlapping size distributions with other microvesicles or macromolecular complexes. Furthermore, centrifugation may provide insufficient means to separate vesicles based on their sizes. However, sequential centrifugations, when combined with sucrose gradient ultracentrifugation, can provide high enrichment of exosomes.

Isolation of exosomes based on size, using alternatives to the ultracentrifugation routes, is another option. Successful purification of exosomes using ultrafiltration procedures that are less time consuming than ultracentrifugation, and do not require use of special equipment have been reported. Similarly, a commercial kit is available (EXOMIR™, Bioo Scientific) which allows removal of cells, platelets, and cellular debris on one microfilter and capturing of vesicles bigger than 30 nm on a second microfilter using positive pressure to drive the fluid. However, for this process, the exosomes are not recovered, their RNA content is directly extracted from the material caught on the second microfilter, which can then be used for PCR analysis. HPLC-based protocols could potentially allow one to obtain highly pure exosomes, though these processes require dedicated equipment and are difficult to scale up. A significant problem is that both blood and cell culture media contain large numbers of nanoparticles (some non-vesicular) in the same size range as exosomes.

II. TRANSFECTION OF EXOSOMES

The inhibitory RNA or therapeutic protein can be introduced into the exosomes by a number of different techniques, such as electroporation or transfection. In particularly preferred embodiments of the invention, the exosomes are loaded by the use of a transfection reagent.

Electroporation. By this method, a number of holes is made in the exosomes by briefly shocking them with an electric field of 100-200 V/cm. The RNA or protein can enter the exosomes through the holes made by the electric field.

Lipofection. This method can be used to transform exosomes with RNA or proteins via vesicles containing the desired RNA or proteins. The vesicles fuses with the exosomes membrane and the contents of the vesicles and the cells are combined. There are a number of transfection kits in the market, ready for use, e.g., ExoFect™ Exosomes Transfection Kit (Cat. No. EXFT10A-1) from System Biosciences, Inc.; and ExoFectin® sRNA-into-Exosome Kit (Cat. No. P401) from 101 Bio.

Transformation using heat shock. Chilling exosomes in the presence of divalent cations such as $Ca^{2+}$ (in $CaCl_2$) makes their membranes become permeable to RNA or DNA. Exosomes are incubated with the RNA and then briefly heat shocked (e.g., 42° C. for 30-120 seconds), which causes the RNA to enter the cell.

Transfection. Cargo can be transfected into exosomes by combining the cargo with a cationic polymer, such as, for example, DEAE-dextran, poly-L-lysine, modified polyaminoacids (e.g., β-aminoacid-polymers or reversed polyamides), modified polyethylenes (e.g., poly(N-ethyl-4-vinylpyridinium bromide) (PVP)), modified acrylates (e.g., poly(dimethylaminoethyl methylacrylate) (pDMAEMA)), modified amidoamines (e.g., poly(amidoamine) (pAMAM)), modified polybetaaminoesters (PBAE) (e.g., diamine end modified 1,4 butanediol diacrylate-co-5-amino-i-pentanol polymers), dendrimers (e.g., polypropylamine dendrimers or pAMAM based dendrimers), polyimine (e.g., poly(ethyleneimine) (PEI) or poly(propyleneimine)), polyallylamine, sugar backbone based polymers (e.g., cyclodextrin based polymers, dextran based polymers or chitosan), or block polymers consisting of a combination of one or more cationic polymers as mentioned above and of one or more hydrophilic or hydrophobic polymers (e.g., polyethyleneglycole).

III. TREATMENT OF DISEASE

Certain aspects of the present invention provide for treating a patient with exosomes that express or comprise a therapeutic agent or a diagnostic agent. A "therapeutic agent" as used herein is an atom, molecule, or compound that is useful in the treatment of cancer or other conditions. Examples of therapeutic agents include, but are not limited to, drugs, chemotherapeutic agents, therapeutic recombinant proteins, therapeutic antibodies and antibody fragments, toxins, radioisotopes, enzymes, nucleases, hormones, immunomodulators, antisense oligonucleotides, chelators, boron compounds, photoactive agents, and dyes. A "diagnostic agent" as used herein is an atom, molecule, or compound that is useful in diagnosing, detecting, or visualizing a disease. According to the embodiments described herein, diagnostic agents may include, but are not limited to, radioactive substances (e.g., radioisotopes, radionuclides, radiolabels or radiotracers), dyes, contrast agents, fluorescent compounds or molecules, bioluminescent compounds or molecules, enzymes, and enhancing agents (e.g., paramagnetic ions).

In addition to protein- and nucleic acid-based therapeutics, exosomes may be used to deliver small molecule drugs, either alone or in combination with any protein- or nucleic acid-based therapeutic. Exemplary small molecule drugs that are contemplated for use in the present embodiments include, but are not limited to, toxins, chemotherapeutic agents, agents that inhibit the activity of an intracellular protein, agents that activate the activity of intracellular proteins, agents for the prevention of restenosis, agents for treating renal disease, agents used for intermittent claudication, agents used in the treatment of hypotension and shock, angiotensin converting enzyme inhibitors, antianginal agents, anti-arrhythmics, anti-hypertensive agents, antiotensin ii receptor antagonists, antiplatelet drugs, b-blockers b1 selective, beta blocking agents, botanical product for cardiovascular indication, calcium channel blockers, cardiovascular/diagnostics, central alpha-2 agonists, coronary vasodilators, diuretics and renal tubule inhibitors, neutral endopeptidase/angiotensin converting enzyme inhibitors, peripheral vasodilators, potassium channel openers, potassium salts, anticonvulsants, antiemetics, antinauseants, antiparkinson agents, antispasticity agents, cerebral stimulants, agents that can be applied in the treatment of trauma, agents that can be applied in the treatment of Alzheimer disease or dementia, agents that can be applied in the treatment of migraine, agents that can be applied in the treatment of neurodegenerative diseases, agents that can be applied in the treatment of kaposi's sarcoma, agents that can be applied in the treatment of AIDS, cancer chemotherapeutic agents, agents that can be applied in the treatment of immune disorders, agents that can be applied in the treatment of psychiatric disorders, analgesics, epidural and intrathecal anesthetic agents, general, local, regional neuromuscular blocking agents sedatives, preanesthetic adrenal/acth, anabolic steroids, agents that can be applied in the treatment of diabetes, dopamine agonists, growth hormone and analogs, hyperglycemic agents, hypoglycemic agents, oral insulins, large volume parenterals (lvps), lipid-altering agents, metabolic studies and inborn errors of metabolism, nutrients/ amino acids, nutritional lvps, obesity drugs (anorectics), somatostatin, thyroid agents, vasopressin, vitamins, corticosteroids, mucolytic agents, pulmonary anti-inflammatory agents, pulmonary surfactants, antacids, anticholinergics, antidiarrheals, antiemetics, cholelitholytic agents, inflammatory bowel disease agents, irritable bowel syndrome agents, liver agents, metal chelators, miscellaneous gastric secretory agents, pancreatitis agents, pancreatic enzymes, prostaglandins, prostaglandins, proton pump inhibitors, sclerosing agents, sucralfate, anti-progestins, contraceptives, oral contraceptives, not oral dopamine agonists, estrogens, gonadotropins, GNRH agonists, GHRH antagonists, oxytocics, progestins, uterine-acting agents, anti-anemia drugs, anticoagulants, antifibrinolytics, antiplatelet agents, antithrombin drugs, coagulants, fibrinolytics, hematology, heparin inhibitors, metal chelators, prostaglandins, vitamin K, anti-androgens, aminoglycosides, antibacterial agents, sulfonamides, cephalosporins, clindamycins, dermatologics, detergents, erythromycins, anthelmintic agents, antifungal agents, antimalarials, antimycobacterial agents, antiparasitic agents, antiprotozoal agents, antitrichomonads, antituberculosis agents, immunomodulators, immunostimulatory agents, macrolides, antiparasitic agents, corticosteroids, cyclooxygenase inhibitors, enzyme blockers, immunomodulators for rheumatic diseases, metalloproteinase inhibitors, nonsteroidal anti-inflammatory agents, analgesics, antipyretics, alpha adrenergic agonists/blockers, antibiotics, antivirals, beta adrenergic blockers, carbonic anhydrase inhibitors, corticosteroids, immune system regulators, mast cell inhibitors, nonsteroidal anti-inflammatory agents, and prostaglandins.

Exosomes may also be used to deliver diagnostic agents. Exemplary diagnostic agents include, but are not limited to, magnetic resonance image enhancement agents, positron emission tomography products, radioactive diagnostic agents, radioactive therapeutic agents, radio-opaque contrast agents, radiopharmaceuticals, ultrasound imaging agents, and angiographic diagnostic agents.

The term "subject" as used herein refers to any individual or patient to which the subject methods are performed. Generally the subject is human, although as will be appreciated by those in the art, the subject may be an animal Thus other animals, including mammals, such as rodents (including mice, rats, hamsters, and guinea pigs), cats, dogs, rabbits, farm animals (including cows, horses, goats, sheep, pigs, etc.), and primates (including monkeys, chimpanzees, orangutans, and gorillas) are included within the definition of subject.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of chemotherapy, immunotherapy, or radiotherapy, performance of surgery, or any combination thereof.

The term "therapeutic benefit" or "therapeutically effective" as used herein refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

The term "cancer," as used herein, may be used to describe a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, pancreas, prostate, skin, stomach, testis, tongue, or uterus.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Nonetheless, it is also recognized that the present invention may also be used to treat a non-cancerous disease (e.g., a fungal infection, a bacterial infection, a viral infection, a neurodegenerative disease, and/or a genetic disorder).

The terms "contacted" and "exposed," when applied to a cell, are used herein to describe the process by which a therapeutic agent is delivered to a target cell or are placed in direct juxtaposition with the target cell. To achieve cell killing, for example, one or more agents are delivered to a cell in an amount effective to kill the cell or prevent it from dividing.

An effective response of a patient, or a patient's "responsiveness" to treatment, refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

Treatment outcomes can be predicted and monitored and/or patients benefiting from such treatments can be identified or selected via the methods described herein.

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the treatment of disease, the appropriate dosage of a therapeutic composition will depend on the type of disease to be treated, as defined above, the severity and course of the disease, the patient's clinical history and response to the agent, and the discretion of the attending physician. The agent is suitably administered to the patient at one time or over a series of treatments.

Therapeutic and prophylactic methods and compositions can be provided in a combined amount effective to achieve the desired effect. A tissue, tumor, or cell can be contacted with one or more compositions or pharmacological formulation(s) comprising one or more of the agents, or by contacting the tissue, tumor, and/or cell with two or more distinct compositions or formulations. Also, it is contemplated that such a combination therapy can be used in conjunction with chemotherapy, radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

A first anti-cancer treatment (e.g., exosomes that express a recombinant protein or comprise an inhibitory RNA) may be administered before, during, after, or in various combinations relative to a second anti-cancer treatment. The administrations may be in intervals ranging from concurrently to minutes to days to weeks. In embodiments where the first treatment is provided to a patient separately from the second treatment, one would generally ensure that a significant period of time did not expire between the time of each delivery, such that the two compounds would still be able to exert an advantageously combined effect on the patient. In such instances, it is contemplated that one may provide a patient with the first therapy and the second therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a first anti-cancer therapy is "A" and a second anti-cancer therapy is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammall and calicheamicin omegall); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum,* dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2013; Hanibuchi et al., 1998; U.S. Pat. No. 5,824,311). It is contemplated that one or more anti-cancer therapies may be employed with the antibody therapies described herein.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

IV. PHARMACEUTICAL COMPOSITIONS

It is contemplated that exosomes that express or comprise a recombinant protein, inhibitory RNA, and/or small molecule drug can be administered systemically or locally to inhibit tumor cell growth and, most preferably, to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

It is not intended that the present invention be limited by the particular nature of the therapeutic preparation. For example, such compositions can be provided in formulations together with physiologically tolerable liquid, gel, solid carriers, diluents, or excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particular requirements of individual subjects.

Where clinical applications are contemplated, it may be necessary to prepare pharmaceutical compositions comprising inhibitory RNAs and/or exosomes in a form appropriate for the intended application. Generally, pharmaceutical compositions, which can be parenteral formulations, can comprise an effective amount of one or more inhibitory RNAs and/or exosomes and/or additional agents dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition comprising an inhibitory RNA and/or exosomes as disclosed herein, or additional active ingredients is as exemplified by Remington's Pharmaceutical Sciences, 18th Ed., 1990, which is incorporated herein by reference in its entirety for all purposes. Moreover, for animal (e.g., human) administration, it will be understood that preparations should meet sterility, pyrogenicity, general safety, and purity standards as required by the FDA Office of Biological Standards.

Further in accordance with certain aspects of the present invention, the composition suitable for administration may be provided in a pharmaceutically acceptable carrier with or without an inert diluent. As used herein, "pharmaceutically acceptable carrier" includes any and all aqueous solvents (e.g., water, alcoholic/aqueous solutions, ethanol, saline solutions, parenteral vehicles, such as sodium chloride, Ringer's dextrose, etc.), non-aqueous solvents (e.g., fats, oils, polyol (for example, glycerol, propylene glycol, and liquid polyethylene glycol, and the like), vegetable oil, and injectable organic esters, such as ethyloleate), lipids, liposomes, dispersion media, coatings (e.g., lecithin), surfactants, antioxidants, preservatives (e.g., antibacterial or antifungal agents, anti-oxidants, chelating agents, inert gases, parabens (e.g., methylparabens, propylparabens), chlorobutanol, phenol, sorbic acid, thimerosal or combinations thereof), isotonic agents (e.g., sugars and sodium chloride), absorption delaying agents (e.g., aluminum monostearate and gelatin), salts, drugs, drug stabilizers, gels, resins, fillers, binders, excipients, disintegration agents, lubricants, sweetening agents, flavoring agents, dyes, fluid and nutrient replenishers, such like materials and combinations thereof, as would be known to one of ordinary skill in the art. The carrier should be assimilable and includes liquid, semi-solid, i.e., pastes, or solid carriers. In addition, if desired, the compositions may contain minor amounts of auxiliary substances, such as wetting or emulsifying agents, stabilizing agents, or pH buffering agents. The pH and exact concentration of the various components in a pharmaceutical composition are adjusted according to well-known parameters. The proper fluidity can be maintained, for example, by the use of a coating, such as lecithin, by the maintenance of the required particle size in the case of dispersion, and by the use of surfactants.

A pharmaceutically acceptable carrier is particularly formulated for administration to a human, although in certain embodiments it may be desirable to use a pharmaceutically acceptable carrier that is formulated for administration to a non-human animal but that would not be acceptable (e.g., due to governmental regulations) for administration to a human. Except insofar as any conventional carrier is incompatible with the active ingredient (e.g., detrimental to the recipient or to the therapeutic effectiveness of a composition contained therein), its use in the therapeutic or pharmaceutical compositions is contemplated. In accordance with certain aspects of the present invention, the composition is combined with the carrier in any convenient and practical manner, i.e., by solution, suspension, emulsification, admixture, encapsulation, absorption, and the like. Such procedures are routine for those skilled in the art.

Certain embodiments of the present invention may comprise different types of carriers depending on whether it is to be administered in solid, liquid, or aerosol form, and whether it needs to be sterile for the route of administration, such as injection. The compositions can be administered intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing, which are described, for example, in Remington's Pharmaceutical Sciences, 18th Ed., 1990, incorporated herein by reference.

The active compounds can be formulated for parenteral administration, e.g., formulated for injection via the intravenous, intramuscular, sub-cutaneous, or even intraperitoneal routes. As such, the embodiments include parenteral formulations. Typically, such compositions can be prepared as either liquid solutions or suspensions; solid forms suitable for use to prepare solutions or suspensions upon the addition of a liquid prior to injection can also be prepared; and the preparations can also be emulsified.

According to the subject embodiments, the parenteral formulations can include exosomes as disclosed herein along with one or more solute and/or solvent, one or more buffering agent and/or one or more antimicrobial agents, or any combination thereof. In some aspects, the solvent can include water, water-miscible solvents, e.g., ethyl alcohol, liquid polyethylene glycol, and/or propylene glycol, and/or water-immiscible solvents, such as fixed oils including, for example, corn oil, cottonseed oil, peanut oil, and/or sesame oil. In certain versions, the solutes can include one or more antimicrobial agents, buffers, antioxidants, tonicity agents, cryoprotectants and/or lyoprotectants.

Antimicrobial agents according to the subject disclosure can include those provided elsewhere in the subject disclosure as well as benzyl alcohol, phenol, mercurials and/or parabens. Antimicrobial agents can include benzalkonium chloride, benzethonium chloride, benzyl alcohol, bronopol, centrimide, cetylpyridinium chloride, chlorhexidine, chlorobutanol, chlorocresol, chloroxylenol, cresol, ethyl alcohol, glycerin, exetidine, imidurea, phenol, phenoxyethanol, phenylethl alcohol, phenlymercuric nitrate, propylene glycol, and/or thimerosal, or any combination thereof. The antimicrobial agents can, in various aspects, be present in a concentration necessary to ensure sterility as is required for pharmaceutical agents. For example, the agents can be present in bacteriostatic or fungistatic concentrations in preparations, e.g., preparations contained in multiple-dose containers. The agents can, in various embodiments, be preservatives and/or can be present in adequate concentration at the time of use to prevent the multiplication of microorganisms, such as microorganisms inadvertently introduced into the preparation while, for example, withdrawing a portion of the contents with a hypodermic needle and syringe. In various aspects, the agents have maximum volume and/or concentration limits (e.g., phenylmercuric nitrate and thimerosal 0.01%, benzethonium chloride and benzalkonium chloride 0.01%, phenol or cresol 0.5%, and chlorobutanol 0.5%). In various instances, agents such as phenylmercuric nitrate, are employed in a concentration of 0.002%. Methyl p-hydroxybenzoate 0.18% and propyl p-hydroxybenzoate 0.02% in combination, and benzyl alcohol 2% also can be applied according to the embodiments. The antimicrobial agents can also include hexylresorcinol 0.5%, phenylmercuric benzoate 0.1%, and/or therapeutic compounds.

Antioxidants according to the subject disclosure can include ascorbic acid and/or its salts, and/or the sodium salt of ethylenediaminetetraacetic acid (EDTA). Tonicity agents as described herein can include electrolytes and/or mono- or disaccharides. Cryoprotectants and/or lyoprotectants are additives that protect biopharmaceuticals from detrimental effects due to freezing and/or drying of the product during freezedry processing. Cryoprotectants and/or lyoprotectants can include sugars (non-reducing) such as sucrose or trehalose, amino acids such as glycine or lysine, polymers such as liquid polyethylene glycol or dextran, and polyols such as mannitol or sorbitol all are possible cryo- or lyoprotectants. The subject embodiments can also include antifungal agents such as butyl paraben, methyl paraben, ethyl paraben, propyl paraben, benzoic acid, potassium sorbate, sodium benzoate, sodium propionate, and/or sorbic acid, or any combination thereof. Additional solutes and antimicrobial agents, buffers, antioxidants, tonicity agents, cryoprotectants and/or lyprotectants and characteristics thereof which may be employed according to the subject disclosure, as well as aspects of methods of making the subject parenteral formulations are described, for example, in Remington's Pharmaceutical Sciences, 21st Ed., 2005, e.g., Chapter 41, which is incorporated herein by reference in its entirety for all purposes.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The therapeutics may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid and the like. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine and the like. Upon formulation, solutions will be administered in a manner compatible with the dosage formulation and in such amount as is therapeutically effective. The formulations are easily administered in a variety of dosage forms, such as formulated for parenteral administrations, such as injectable solutions, or aerosols for delivery to the lungs, or formulated for alimentary administrations, such as drug release capsules and the like.

In a specific embodiment of the present invention, the composition is combined or mixed thoroughly with a semisolid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in a composition include buffers, amino acids, such as glycine and lysine, carbohydrates, such as dextrose, mannose, galactose, fructose, lactose, sucrose, maltose, sorbitol, mannitol, etc.

In further embodiments, the present invention may concern the use of a pharmaceutical lipid vehicle composition comprising one or more lipids and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present invention administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above.

V. RECOMBINANT PROTEINS AND INHIBITORY RNAS

Some embodiments concern recombinant proteins and polypeptides. Particular embodiments concern a recombinant protein or polypeptide that exhibits at least one therapeutic activity. In some embodiments, a recombinant protein or polypeptide may be a therapeutic antibody. In some aspects, a therapeutic antibody may be an antibody that specifically or selectively binds to an intracellular protein. In further aspects, the protein or polypeptide may be modified to increase serum stability. Thus, when the present application refers to the function or activity of "modified protein" or a "modified polypeptide," one of ordinary skill in the art would understand that this includes, for example, a protein or polypeptide that possesses an additional advantage over the unmodified protein or polypeptide. It is specifically contemplated that embodiments concerning a "modified protein" may be implemented with respect to a "modified polypeptide," and vice versa.

In some aspects, a therapeutic recombinant protein may be a protein having an activity that has been lost in a cell of the patient, a protein having a desired enzymatic activity, a protein having a desired inhibitory activity, etc. For example, the protein may be a transcription factor, an enzyme, a proteinaceous toxin, an antibody, a monoclonal antibody, etc.

As exosomes are known to comprise the machinery necessary to complete mRNA transcription and protein translation (see PCT Publication No. WO2015/085096, which is incorporated herein by reference in its entirety), mRNA or DNA nucleic acids encoding a therapeutic protein may be transfected into exosomes. Alternatively, the therapeutic protein itself may be transfected into the exosomes. Exemplary therapeutic proteins include, but are not limited to, a tumor suppressor protein, peptides, a wild type protein counterparts of a mutant protein, a DNA repair protein, a proteolytic enzyme, proteinaceous toxin, a protein that can inhibit the activity of an intracellular protein, a protein that can activate the activity of an intracellular protein, or any protein whose loss of function needs to be reconstituted.

One specific type of protein that it may be desirable to introduce into the intracellular space of a diseased cell is an antibody (e.g., a monoclonal antibody). Such an antibody may specifically or selectively bind to an intracellular antigen, thereby disrupting the function of an intracellular protein and/or disrupt an intracellular protein-protein interaction. Exemplary targets of such monoclonal antibodies include, but are not limited to, proteins involved in the RNAi pathway, telomerase, transcription factors that control disease processes, kinases, phosphatases, proteins required for DNA synthesis, and proteins required for protein translation. In addition to monoclonal antibodies, any antigen binding fragment thereof, such as a scFv, a Fab fragment, a Fab', a F(ab')2, a Fv, a peptibody, a diabody, a triabody, or a minibody, is also contemplated. Any such antibodies or antibody fragment may be either glycosylated or aglycosylated.

Recombinant proteins may possess deletions and/or substitutions of amino acids; thus, a protein with a deletion, a protein with a substitution, and a protein with a deletion and a substitution are modified proteins. In some embodiments, these proteins may further include insertions or added amino acids, such as with fusion proteins or proteins with linkers, for example. A "modified deleted protein" lacks one or more residues of the native protein, but may possess the specificity and/or activity of the native protein. A "modified deleted protein" may also have reduced immunogenicity or antigenicity. An example of a modified deleted protein is one that has an amino acid residue deleted from at least one antigenic region that is, a region of the protein determined to be antigenic in a particular organism, such as the type of organism that may be administered the modified protein.

Substitution or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a control polypeptide are included, provided the biological activity of the protein is maintained. A recombinant protein may be biologically functionally equivalent to its native counterpart in certain aspects.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide," and "peptide are used interchangeably herein.

As used herein, an "amino acid residue" refers to any naturally occurring amino acid, any amino acid derivative, or any amino acid mimic known in the art. In certain embodiments, the residues of the protein or peptide are sequential, without any non-amino acids interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid.

Certain embodiments of the present invention concern fusion proteins. These molecules may have a therapeutic protein linked at the N- or C-terminus to a heterologous domain. For example, fusions may also employ leader sequences from other species to permit the recombinant expression of a protein in a heterologous host. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

In a particular embodiment, the therapeutic protein may be linked to a peptide that increases the in vivo half-life, such as an XTEN polypeptide (Schellenberger et al., 2009), IgG Fc domain, albumin, or albumin binding peptide.

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

siNA (e.g., siRNA) are well known in the art. For example, siRNA and double-stranded RNA have been described in U.S. Pat. Nos. 6,506,559 and 6,573,099, as well as in U.S. Patent Applications 2003/0051263, 2003/0055020, 2004/0265839, 2002/0168707, 2003/0159161, and 2004/0064842, all of which are herein incorporated by reference in their entirety.

Within a siNA, the components of a nucleic acid need not be of the same type or homogenous throughout (e.g., a siNA may comprise a nucleotide and a nucleic acid or nucleotide analog). Typically, siNA form a double-stranded structure; the double-stranded structure may result from two separate nucleic acids that are partially or completely complementary. In certain embodiments of the present invention, the siNA may comprise only a single nucleic acid (polynucleotide) or nucleic acid analog and form a double-stranded structure by complementing with itself (e.g., forming a hairpin loop). The double-stranded structure of the siNA may comprise 16, 20, 25, 30, 35, 40, 45, 50, 60, 65, 70, 75, 80, 85, 90, 100, 150, 200, 250, 300, 350, 400, 450, 500 or more contiguous nucleobases, including all ranges therein. The siNA may comprise 17 to 35 contiguous nucleobases, more preferably 18 to 30 contiguous nucleobases, more preferably 19 to 25 nucleobases, more preferably 20 to 23 contiguous nucleobases, or 20 to 22 contiguous nucleobases, or 21 contiguous nucleobases that hybridize with a complementary nucleic acid (which may be another part of the same nucleic acid or a separate complementary nucleic acid) to form a double-stranded structure.

Agents of the present invention useful for practicing the methods of the present invention include, but are not limited to siRNAs. Typically, introduction of double-stranded RNA (dsRNA), which may alternatively be referred to herein as small interfering RNA (siRNA), induces potent and specific gene silencing, a phenomena called RNA interference or RNAi. RNA interference has been referred to as "cosuppression," "post-transcriptional gene silencing," "sense suppression," and "quelling." RNAi is an attractive biotechnological tool because it provides a means for knocking out the activity of specific genes.

In designing RNAi there are several factors that need to be considered, such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Preferably the siRNA exhibits greater than 80%, 85%, 90%, 95%, 98%, or even 100% identity between the sequence of the siRNA and the gene to be inhibited. Sequences less than about 80% identical to the target gene are substantially less effective. Thus, the greater homology between the siRNA and the gene to be inhibited, the less likely expression of unrelated genes will be affected.

In addition, the size of the siRNA is an important consideration. In some embodiments, the present invention relates to siRNA molecules that include at least about 19-25 nucleotides and are able to modulate gene expression. In the context of the present invention, the siRNA is preferably less than 500, 200, 100, 50, or 25 nucleotides in length. More preferably, the siRNA is from about 19 nucleotides to about 25 nucleotides in length.

A target gene generally means a polynucleotide comprising a region that encodes a polypeptide, or a polynucleotide region that regulates replication, transcription, or translation or other processes important to expression of the polypeptide, or a polynucleotide comprising both a region that encodes a polypeptide and a region operably linked thereto that regulates expression. Any gene being expressed in a cell can be targeted. Preferably, a target gene is one involved in or associated with the progression of cellular activities important to disease or of particular interest as a research object.

siRNA can be obtained from commercial sources, natural sources, or can be synthesized using any of a number of techniques well-known to those of ordinary skill in the art. For example, one commercial source of predesigned siRNA is Ambion®, Austin, Tex. Another is Qiagen® (Valencia, Calif.). An inhibitory nucleic acid that can be applied in the compositions and methods of the present invention may be any nucleic acid sequence that has been found by any source to be a validated downregulator of a protein of interest. Without undue experimentation and using the disclosure of this invention, it is understood that additional siRNAs can be designed and used to practice the methods of the invention.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In certain aspects, the RNA molecule contains a 3'-hydroxyl group. Nucleotides in the RNA molecules of the present invention can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Application Publication 2004/0019001 and U.S. Pat. No. 6,673,611 (each of which is incorporated by reference in its entirety). Collectively, all such altered nucleic acids or RNAs described above are referred to as modified siRNAs.

As exosomes are known to comprise DICER and active RNA processing RISC complex (see PCT Publication No. WO2014/152622, which is incorporated herein by reference in its entirety), shRNA transfected into exosomes can mature into RISC-complex bound siRNA within the exosomes themselves. Alternatively, mature siRNA can itself be transfected into exosomes or liposomes. Thus, by way of example, the following are classes of possible target genes that may be used in the methods of the present invention to modulate or attenuate target gene expression: wild-type or mutant versions of developmental genes (e.g., adhesion molecules, cyclin kinase inhibitors, Wnt family members, Pax family members, Winged helix family members, Hox family members, cytokines/lymphokines and their receptors, growth or differentiation factors and their receptors, neurotransmitters and their receptors), tumor suppressor genes, pro-apoptotic genes, oncogenes, and enzymes. In some cases, sh/siRNA may be designed to specifically target a mutant version of a gene expressed in a cancer cell while not affecting the expression of the corresponding wild-type version. In fact, any inhibitory nucleic acid that can be applied in the compositions and methods of the present invention if such inhibitory nucleic acid has been found by any source to be a validated downregulator of a protein of interest.

VI. Kits and Diagnostics

In various aspects of the invention, a kit is envisioned containing the necessary components to purify exosomes from a body fluid, tissue culture medium, or fruit product. In other aspects, a kit is envisioned containing the necessary components to isolate exosomes and transfect them with a therapeutic nucleic acid, therapeutic protein, or a nucleic acid encoding a therapeutic protein therein.

The kit may comprise one or more sealed vials containing any of such components. In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill. The instruction information may be in a computer readable media containing machine-readable instructions that, when executed using a computer, cause the display of a real or virtual procedure of purifying exosomes from a sample and transfecting a therapeutic nucleic acid therein, expressing a recombinant protein therein, or transfecting a recombinant protein therein.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Generation of HEXPO Nanoparticles Using Naturally Occurring Exosomes To generate large quantities of exosomes for therapeutic purposes, cells were isolated from SV40 immortal mice. This is an ideal model for obtaining exosomes from normal cell lines since the SV40 virus can be fully inactivated after incubation of these cells at 37° C. for 2 days. Many cell lines (e.g., fibroblasts, macrophages, dendritic cells) have already been isolated from these mice, and the amount of exosomes produced by each cell type (FIG. 1A) along with their cell penetration potential was systematically assessed (FIG. 1B). Cancer cells and normal fibroblasts produced large amounts of exosomes that were readily taken up by recipient cells.

Figure 2A:
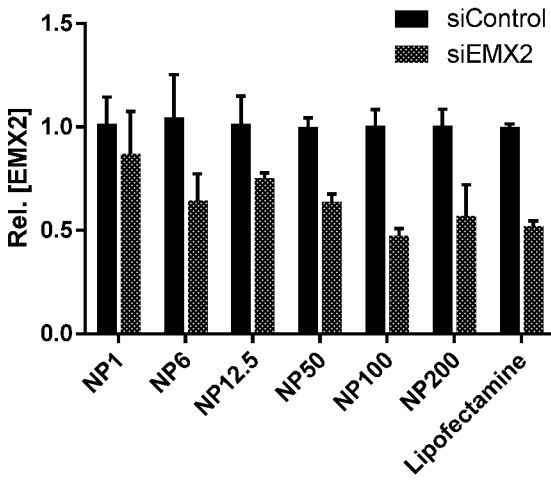
FIGS. 2A-B. Transfection efficiency and toxicity profile of polyplexes at different nitrogen:phosphate (N:P) ratios. MOEC cells were treated with siRNAs that were complexes with dendrimers at different N:P ratios.
Figure 2B:
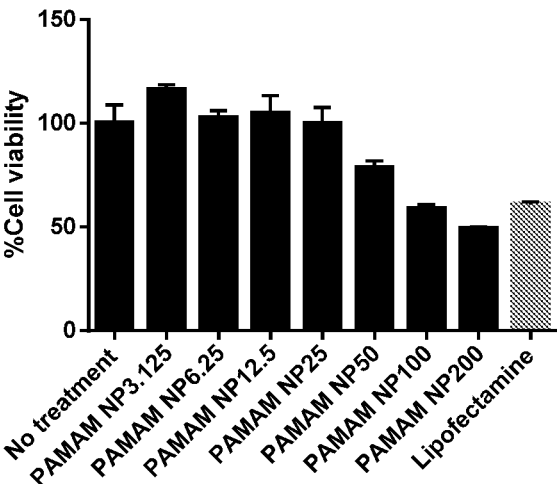
Figure 3:
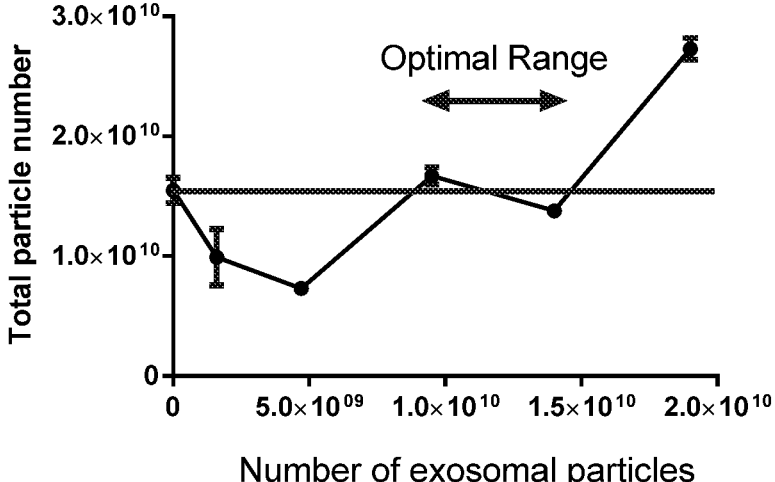
FIG. 3. Number of exosomal particles required to coat polyplexes containing 15 μg of siRNA. Excess exosomal particles were observed when >1.5×10$^{10}$ exosomes were added to the formulation Minimum of 1×10$^{10}$ exosomes is required to maintain particle integrity.

To facilitate efficient loading of RNAi nucleotides into exosomes, a slightly positively charged siRNA-containing polymeric core was formulated using either PAMAM dendrimers, chitosan, or protamine. All of these polymers complex with RNAi nucleotides with high efficiency (>95%). The optimal polymer to nucleic acid ratios were determined based on toxicity and efficacy (FIGS. 2A-B). The polyplexes were subsequently added to exosomal suspension at a defined ratio (FIG. 3). Using flow cytometry and stem-loop PCR, the resultant HEXPO nanoparticles were found to have a siRNA loading efficiency of >95%, representing a significant advance over traditional methods of loading RNAi therapeutics into exosomes (e.g., electroporation). While chemical loading of RNAi nucleotides into exosomes has been described (e.g., with the use of Exofect or Lipofectamine), formulations prepared using these existing methods have a large particle size distribution that limits their use in vivo (FIG. 4). The true loading efficiency of these formulations is also difficult to assess as the exosomes precipitation reagent (one of the reagents used to prepare ExoFect-loaded exosomes) would pull down non-exosomes products (FIG. 5).

In contrast to the particles prepared using Exofect or Lipofectamine, HEXPO nanoparticles exhibit uniform particle size distribution that is suitable for in vivo applications (FIG. 4) and a superior toxicity profile (FIG. 6). These HEXPO nanoparticles are slightly negatively charged (−5 mV) and are ~135 nm in size. To demonstrate RNAi delivery into cells, EphA2 siRNA was loaded into HEXPO nanoparticles and >70% target gene knockdown was achieved in ovarian cancer cells (FIG. 7A). These HEXPO nanoparticles are capable of accumulating in tumors after i.v. administration in orthotopic mouse models of ovarian cancer. PEGy-lated liposomes (<100 nm) formulated using neutral lipids (EPC) and PEG2000-DSPE were used as a reference control in this experiment. Both formulations displayed a similar degree of tumor localization (FIG. 7B). Given that PEGy-lation can hinder cell uptake, the intrinsic ability of HEXPO nanoparticles to localize in tumors, along with the ease of engineering exosomal membranes for optimal tumor target-ing, make HEXPO carriers an attractive platform for deliv-ering RNAi therapeutics. It was further demonstrated that coating of HEXPO nanoparticles using exosomal mem-branes is crucial for the ability of HEXPO nanoparticles to deliver siRNAs to tumors (FIG. 8). The ability of HEXPO nanoparticles to penetrate tumors was assessed by treating mice bearing ID8 tumors with one dose of Cy3-siRNA containing HEXPO nanoparticles (i.p., 5 µg siRNA). Fluo-rescence microscopy was used to identify the location of siRNAs in tumors 24 hours post treatment. These data showed that HEXPO nanoparticles can penetrate deep into the tumor tissue (FIG. 9), resulting in efficient gene silencing in vivo (FIG. 10).

To further enhance the clinical translatability of these HEXPO nanoparticles, siRNA-loaded HEXPO particles were formulated in the presence of sucrose, a lyoprotectant. Different amounts of sucrose were added to the formulations before freeze-drying and the particle size was assessed upon hydration with water. At the optimal sucrose:nucleic acid ratio (i.e., isotonic when reconstituted), the resultant particle size was approximately 100 nm and the final hydrated product was isotonic and could be injected into mice without further processing (FIG. 11). Thus, this formulation process provides a platform for scaling up the HEXPO production with final products suitable for long-term storage.

Example 2—Generation of HEXPO Nanoparticles Using Plant-Derived Exosomes

Despite the promise of using exosomes derived from immortal mice, culturing large number of cells in vitro is quite labor-intensive, and the potential immunogenicity of these murine exosomes in humans is currently unknown. Therefore, other potential sources of exosomes that are inexpensively obtained and safe for use in humans were investigated. Among many possible sources, edible veg-etables and plants are promising alternatives for exosomes production. On a per-dollar basis, the amount of exosomes that can be obtained from fruit is approximately 40,000-fold higher compared with cells cultured in exosomes-free media (FIG. 12A). By purifying fruit-derived exosomes using a sucrose gradient column, the potential concern of isolating non-exosomes impurities, which would typically arise from the gradient ultracentrifugation method, was overcome. The final purified exosomes were ~100 nm, and HEXPO nan-oparticles with high siRNA loading efficiency were able to be synthesized using these exosomes (FIG. 12B). These HEXPO nanoparticles were also able to deliver siRNAs efficiently into cells (FIG. 12C).

All of the methods disclosed and claimed herein can be made and executed without undue experimentation in light of the present disclosure. While the compositions and meth-ods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. Nos. 4,870,287
5,739,169
5,760,395
5,801,005
5,824,311
5,830,880
5,846,945
6,506,559
6,573,099
6,673,611
U.S. Application Publication 2002/0168707
U.S. Application Publication 2003/0051263
U.S. Application Publication 2003/0055020
U.S. Application Publication 2003/0159161
U.S. Application Publication 2004/0019001
U.S. Application Publication 2004/0064842
U.S. Application Publication 2004/0265839
Alvarez-Erviti et al., Delivery of siRNA to the mouse brain by systemic injection of targeted exosomes. *Nature Biotechnology,* 29:341-345, 2011.
Austin-Ward and Villaseca, Gene therapy and its appli-cations. *Rev. Med. Chil.,* 126:838-845, 1998.
Bukowski et al., Signal transduction abnormalities in T lymphocytes from patients with advanced renal carci-noma: clinical relevance and effects of cytokine therapy. *Clin. Cancer Res.,* 4:2337-2347, 1998.
Christodoulides et al., Immunization with recombinant class 1 outer-membrane protein from *Neisseria menin-gitidis*: influence of liposomes and adjuvants on anti-body avidity, recognition of native protein and the induction of a bactericidal immune response against meningococci. *Microbiology,* 144:3027-3037, 1998.
Combes et al., A new flow cytometry method of platelet-derived microvesicle quantitation in plasma, *Thromb. Haemost.,* 77:220, 1997.
Cooper et al., Systemic exosomal siRNA delivery reduced alpha-synuclein aggregates in brains of transgenic mice. *Movement Disorders,* 29:1476-1485, 2014.
Davidson et al., Intralesional cytokine therapy in cancer: a pilot study of GM-CSF infusion in mesothelioma. *J. Immunother.,* 21:389-398, 1998.
Hanibuchi et al., Therapeutic efficacy of mouse-human chimeric anti-ganglioside GM2 monoclonal antibody against multiple organ micrometastases of human lung cancer in NK cell-depleted SCID mice. *Int. J. Cancer,* 78:480-485, 1998.
Hellstrand et al., Histamine and cytokine therapy. *Acta Oncol.,* 37:347-353, 1998.
Hollander, Immunotherapy for B-cell lymphoma: current status and prospective advances. *Front Immunol.,* 3:3, 2013.
Hui and Hashimoto, Pathways for Potentiation of Immu-nogenicity during Adjuvant-Assisted Immunizations with *Plasmodium falciparum* Major Merozoite Surface Protein I. *Infec. Immun.,* 66:5329-5336, 1998.

Kooijmans et al., Electroporation-induced siRNA precipitation obscures the efficiency of siRNA loading into extracellular vesicles. *J. Control Release,* 172:229-238, 2013.

Losche et al., Platelet-derived microvesicles transfer tissue factor to monocytes but not to neutrophils. *Platelets,* 15:109-115, 2004.

Mesri and Altieri, Endothelial cell activation by leukocyte microparticles. *J. Immunol.,* 161:4382-4387, 1998.

Morel et al., Cellular microparticles: a disseminated storage pool of bioactive vascular effectors. *Curr. Opin. Hematol.,* 11: 156-164, 2004.

PCT Publication No. WO2012/070324

PCT Publication No. WO2014/152622

PCT Publication No. WO2015/085096

Qin et al., Interferon-beta gene therapy inhibits tumor formation and causes regression of established tumors in immune-deficient mice. *Proc. Natl. Acad. Sci. U.S.A.,* 95:14411-14416, 1998.

Remington's Pharmaceutical Sciences, 18th Ed., 1990

Schellenberger et al., A recombinant polypeptide extends the in vivo half-life of peptides and proteins in a tunable manner Nat. *Biotechnol.,* 27:1186-1190, 2009.

The invention claimed is:

1. A pharmaceutical composition comprising a lipid-based nanoparticle and an excipient, wherein the lipid-based nanoparticle comprises (a) a core comprising a cationic polymer, wherein the cationic polymer is G3-PAMAM, G4-PAMAM, chitosan, or protamine, and a therapeutic agent and (b) a lipid coating comprising an exosome-derived membrane, wherein the therapeutic agent is a nucleic acid, a therapeutic protein, an antibody, or a small molecule drug, and wherein the lipid-based nanoparticles have a uniform particle size distribution.

2. The composition of claim 1, wherein the lipid-based nanoparticle is an exosome.

3. The composition of claim 2, wherein the therapeutic agent is a nucleic acid, and wherein the exosome: nucleic acid ratio is about 10-15 billion exosomal particles per 15 μg of nucleic acid.

4. The composition of claim 2, wherein the exosome is isolated from breast milk.

5. The composition of claim 2, wherein the exosome is isolated from a mammalian cell or a plant.

6. The composition of claim 5, wherein the plant is a fruit.

7. The composition of claim 6, wherein the fruit is a watermelon.

8. The composition of claim 1, wherein the nucleic acid is an inhibitory RNA.

9. The composition of claim 1, wherein at least 95% of the lipid-based nanoparticles in the composition are loaded with the therapeutic agent.

10. A pharmaceutical composition comprising (i) a transfected exosome made by (a) incubating a therapeutic agent with a cationic polymer to produce a polyplex, wherein the cationic polymer is G3-PAMAM, G4-PAMAM, chitosan, or protamine; and (b) incubating the polyplex with isolated exosomes, and (ii) an excipient, wherein the therapeutic agent is a nucleic acid, a therapeutic protein, an antibody, or a small molecule drug, wherein the transfected exosomes have a uniform particle size distribution.

11. The composition of claim 10, wherein the isolated exosomes are isolated from mammalian cells, plant cells, or breast milk.

12. The composition of claim 10, wherein the nucleic acid is an inhibitory RNA.

13. The composition of claim 10, wherein the therapeutic agent is a nucleic acid, and wherein the exosome: nucleic acid ratio is about 10-15 billion exosomal particles per 15 μg of nucleic acid.

14. The composition of claim 10, wherein the transfected exosomes are about 135 nm in diameter.

15. The composition of claim 10, wherein at least 95% of the transfected exosomes in the composition are loaded with the therapeutic agent.

16. A method of treating a disease in a patient in need thereof comprising administering a composition of claim 10 to the patient, thereby treating the disease in the patient.

* * * * *